(12) United States Patent
Guzak et al.

(10) Patent No.: US 9,329,758 B2
(45) Date of Patent: May 3, 2016

(54) MULTIPLE SENSORY CHANNEL APPROACH FOR TRANSLATING HUMAN EMOTIONS IN A COMPUTING ENVIRONMENT

(71) Applicants: Barbara S. Guzak, Coppell, TX (US); Hung-Tack Kwan, Coppell, TX (US); Janki Y. Vora, Coppell, TX (US)

(72) Inventors: Barbara S. Guzak, Coppell, TX (US); Hung-Tack Kwan, Coppell, TX (US); Janki Y. Vora, Coppell, TX (US)

(73) Assignee: International Business Machines Corporation, Armonk, NY (US)

(*) Notice: Subject to any disclaimer, the term of this patent is extended or adjusted under 35 U.S.C. 154(b) by 60 days.

(21) Appl. No.: 14/071,148

(22) Filed: Nov. 4, 2013

(65) Prior Publication Data

US 2014/0068472 A1 Mar. 6, 2014

Related U.S. Application Data

(63) Continuation of application No. 12/540,735, filed on Aug. 13, 2009, now abandoned.

(51) Int. Cl.

| | |
|---|---|
| *G06F 3/041* | (2006.01) |
| *G06F 3/0484* | (2013.01) |
| *A61B 5/16* | (2006.01) |
| *A61B 5/00* | (2006.01) |
| *A61B 5/01* | (2006.01) |
| *A61B 5/04* | (2006.01) |
| *A61B 5/053* | (2006.01) |

(52) U.S. Cl.
CPC ............... *G06F 3/0484* (2013.01); *A61B 5/16* (2013.01); *A61B 5/165* (2013.01); *A61B 5/6804* (2013.01); *A61B 5/01* (2013.01); *A61B 5/04008* (2013.01); *A61B 5/0531* (2013.01)

(58) Field of Classification Search
CPC ........ A61B 5/16; A61B 5/165; A61B 5/0533; G06F 17/30; G06F 17/30017; G06F 13/00
USPC .............. 455/566; 706/46, 229; 709/213, 219
See application file for complete search history.

(56) References Cited

U.S. PATENT DOCUMENTS

| | | | |
|---|---|---|---|
| 2005/0261032 A1 | 11/2005 | Seo et al. | |
| 2006/0036751 A1 | 2/2006 | Garbow et al. | |
| 2008/0215617 A1 | 9/2008 | Cecchi et al. | |
| 2009/0164403 A1 | 6/2009 | Jung et al. | |

FOREIGN PATENT DOCUMENTS

DE 102004001801 A1 7/2005

*Primary Examiner* — Melanie Hand
(74) *Attorney, Agent, or Firm* — Steven M. Greenberg, Esq.; CRGO Law

(57) ABSTRACT

Sensory inputs of a user can be received by a computing device. At least one of the sensory inputs can include a physiological input providing a physiological measurement from a body of the user. Each sensory input can be processed in a unique one of a set of standards-defined sensory channels, each corresponding to a specific emotion dimension. Processing the sensory inputs can transform the physiological measurement into an emotion dimension value. The emotion dimension values from each of the sensory channels can be aggregated to generate at least one emotion datum value, which is a standards-defined value for an emotional characteristic of the user. Historical data for a user can be optionally collected and used by a learning and calibration component to improve the accuracy of the generated emotion datum values for a specific individual. A programmatic action driven by the emotion datum value can be performed.

20 Claims, 3 Drawing Sheets

MULTIPLE SENSORY CHANNEL APPROACH FOR TRANSLATING HUMAN EMOTIONS IN A COMPUTING ENVIRONMENT

CROSS-REFERENCE TO RELATED APPLICATIONS

This application claims the benefit of U.S. application Ser. No. 12/540,735 filed 13 Aug. 2009. The teachings of the parent case (application Ser. No. 12/540,735) are hereby incorporated by reference in their entirety.

BACKGROUND

The present invention relates to the field of human-to-machine interfacing, more particularly to a multisensory channel approach for translating human emotions in a computing environment.

Humans' interactions and interfaces involving machines have been rapidly evolving as computing devices have a continuingly escalating prominence in business and social settings. From a business perspective, virtual meetings save time, expense, and hassle compared to in-person meetings. From an entertainment perspective, on-line virtual spaces (e.g., SECOND LIFE, ACTIVE WORLD, OPENSIM, WORLD OF WARCRAFT, etc.) provide a rich interactive marketplace, which can be customized for preferences of a user. From a socialization perspective, computing devices have been pervasively enabling family and friends to maintain contact with one another.

One current weakness with interactions between humans and machines relates to emotional expressiveness. A common way for communicating emotions within electronic correspondence is to type a description of emotions within plain text, often preceded with an "emote" tag. Emoticons, which are icons or graphics denoting specific emotions, can also be used to exchange emotions within electronic correspondence.

Existing emotion conveyance techniques lack low level application integration and generally exist within a distinct communication channel isolated from the remainder of a running application. Additionally, today's emotion conveyance techniques are manually driven by a user, requiring explicit user input conveying a user's emotional state. Humans, however, are often reluctant to honestly convey their emotional state with others, even if capable of an accurate self-assessment of emotional state, which can be problematic as well.

BRIEF SUMMARY

One aspect of the disclosure includes a method and computer program product for incorporating human emotions in a computing environment. In this aspect, sensory inputs of a user can be received by a computing device. At least one of the sensory inputs can include a physiological input providing a physiological measurement from a body of the user. Each sensory input can be processed in a unique one of a set of standards-defined sensory channels, each corresponding to a specific emotion dimension. Processing the sensory inputs can transform the physiological measurement into an emotion dimension value. The emotion dimension values from each of the sensory channels can be aggregated to generate at least one emotion datum value, which is a standards-defined value for an emotional characteristic of the user. The emotion datum value can be a value independent of any sensory capture device and independent of any single one of the standards-defined sensory channels. A programmatic action driven by the emotion datum value can be performed.

Another aspect of the disclosure is for a system for incorporating human emotions in a computing environment. The system can include a set of discrete sensory channels, a set of in-channel processors, and a sensory aggregator. Each of the discrete sensory channels can be a standards-defined sensory channel corresponding to a specific emotion dimension. Sensory input handled within the sensory channels can include physiological input providing a physiological measurement from a body of the user. The in-channel processors can process sensory input specific to the channel and can generate emotion dimension values from the sensory input. Each emotion dimension value can be one that has been transformed to be independent of idiosyncrasies of a sensory capture device from which the sensory input was originally obtained. The sensory aggregator can aggregate emotion dimension values generated in a per-channel basis by the in-channel processors to generate at least one emotion datum value. The emotion datum value can be a standards-defined value for an emotional characteristic of a user from whom the sensory input was gathered. The emotion datum value can be a value independent of any single one of the standards-defined sensory channels and can be an application independent value that is able to be utilized by a set of independent applications to discern emotions of the user and to cause application specific code of the independent applications to be reactive to changes in sensory aggregator generated emotion datum values.

DETAILED DESCRIPTION

Figure 1:
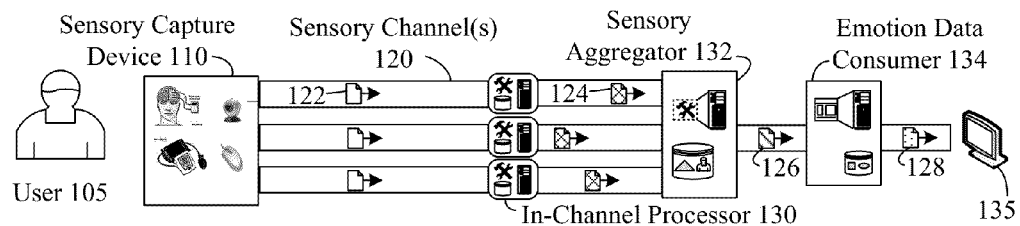
FIG. 1 shows use of multiple sensory channels that process raw sensory inputs, which are aggregated to translate human emotions into a computing environment in accordance with an embodiment of the inventive arrangements disclosed herein.
Figure 1:
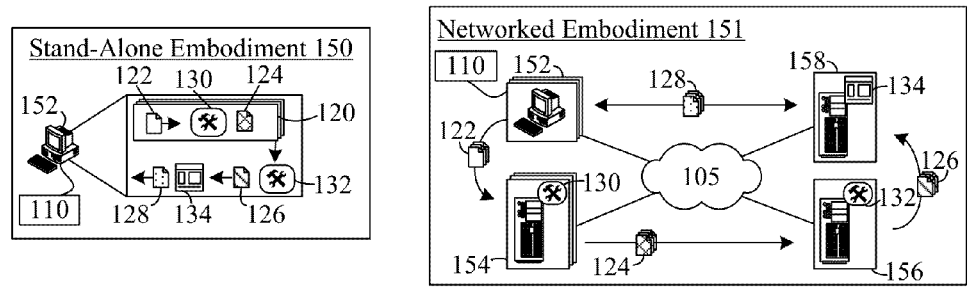
Figure 1:
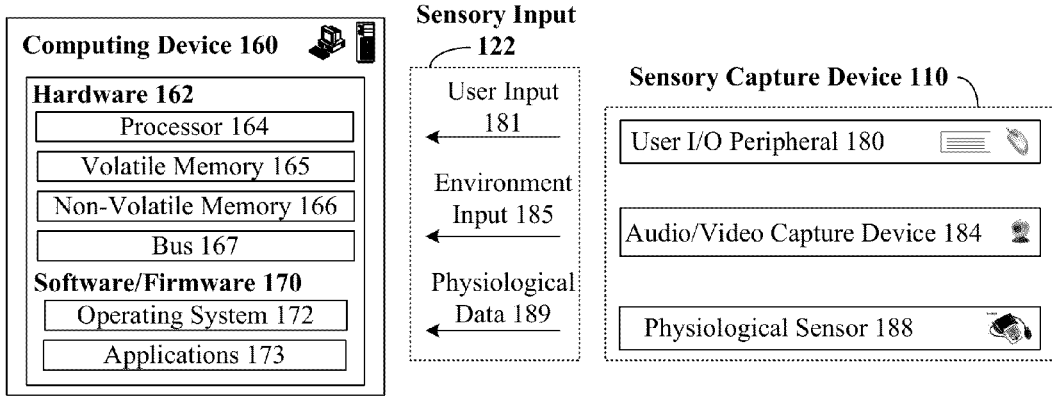

This disclosure provides an approach for translating human emotions in a computing environment, where the approach utilizes multiple sensory channels. Each sensory channel can be associated with a specific raw input, which can be processed in-channel. The raw input can include physiological data (e.g., brain signal readings, heart rate, blood pressure, etc.) captured by physiological sensors, input manually entered by a user via a peripheral (keyboard, mouse, microphone, etc.), and other environmental inputs (e.g., video, audio, etc.) gathered by capture devices. Input can be optionally processed to filter out abnormalities, to normalize human specific input to a baseline values, and to abstract sensory data from specifics of a capture device, thereby converting sensory channel input into a device independent form. Results from each sensory channel can be aggregated to determine a current emotional state of a user. Aggregated emotional information can be fed into one or more user interactive applications, which can programmatically react to the emotional information, thus providing an ability to tailor output and programmatic responds to a user's emotional state.

Historically, accessing human emotions via computer program products has occurred in an ad hoc manner using proprietary processing techniques. In contrast, the disclosure provides a systematic and extensible framework capable of adapting and refining itself as new emotion capture devices and analysis techniques emerge. Use of multiple different sensory channels provides a scalable solution, which is adaptable for a variety of different physiological sensors and other sensory capture devices. Initial processing of raw data can be handled by special purpose analysis engines, which may exist remote from a computing device with which a user interacts. An ability to remotely process discrete sensory channels is significant, as some analysis processes (e.g., facial expression analysis, voice stress analysis, semantic analysis of manually input content, etc.) for ascertaining user emotions can include resource intensive computing operations. In one embodiment, in-channel processing of input and/or aggregation of input from multiple channels can be performed as a software service, such as a Web service.

Processed output per sensory channel can be quantified in a discrete, manageable, and standardized format. Channel specific input can be further processed by a sensory aggregator, which can accept standardized channel input. The sensory aggregator can combine and weigh the per channel inputs to produce aggregate emotional data, which can also conform to a defined standard. For example, a universal format can be established for various emotions, which can be fed into an application in an easy to consume, standardized fashion. Thus, in a series of defined, repeatable, scalable, and standardized stages, complex raw sensory input can be captured, processed, aggregated, and distilled into a standardized usable format able to be consumed by emotion-reactive applications.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 1 shows use of multiple sensory channels 120 that process raw sensory inputs 122, which are aggregated to translate human emotions into a computing environment in accordance with an embodiment of the inventive arrangements disclosed herein. More specifically, one or more sensory capture devices 110 can capture raw (or pre-processed) sensory input 122 from a user 105. Each distinct sensory input 122 can be initially handled within a distinct sensory channel 120, where an in-channel processor 130 can transform the sensory input 122 to processed input 124 accepted by a sensory aggregator 132. Hence, the in-channel processor 130 can receive raw (minimally processed, or pre-processed) sensory data 122 and can produce channel processed input 124.

In one embodiment, the input 122 can be pushed (from a sensory capture device 110) to the in-channel processor 130, although pull (from processor 130) based embodiments are also contemplated, as are embodiments where an intermediary data cache is established between the sensory capture device 110 and processor 130. The sensory data 122 can be received as digital or analog data, where analog data can be converted to a digital form. In one embodiment, the sensory inputs 122 can be optionally sampled, where some types of inputs 122 can require more or less sampling than others. Additionally, an input unit (e.g., a unit or set of data to be processed in a processing cycle) received and/or handled by an in-channel processor 130 can be variable. In one embodiment, the channel processed input 124 can be a change reactive data element, which is only conveyed from the in-channel processor 130 when the generated value is changed from a previously determined value (and/or when a change from a last determined value exceeds an established (but configurable) variance threshold).

The sensory aggregator 132 can use the input 124 to generate standardized emotion data 126, which an emotion data consumer 134 utilizes to produce emotion adjusted output 128 presentable upon output device 135. In one embodiment, sensory aggregator 132 can be triggered each time a new input 124 is received, which results in a new emotion datum 126 instance being selectively generated and pushed to the consumers 134. In another embodiment, aggregator 132 can evaluate newly received inputs 124 in a cyclic fashion and/or responsive to a received update command. Further, embodiments are contemplated where one or more data consumers 134 pull data from aggregator 132, as are embodiments where an intermediary data cache receives datum 126 pushed from aggregator 132, which are later pulled (responsive to cache directed queries) by one or more data consumers 134.

The sensory aggregator 132 can include an algorithm that weights each input 124, where weights are configurable. For example, the aggregator 132 can weigh a voice derived input 124 more heavily than a heart rate input 124, which is weighed more heavily than a facial expression based input 124, which is weighed more heavily than a skin response based input 124, which is weighed more heavily than a brain signal input 124. In one embodiment, aggregator 132 can initially classify inputs 124 as being indicative of either positive emotions (e.g., happy, excited, calm, etc.) or negative emotions (e.g., sad, bored, frantic, etc.), where standardized emotion datum 126 result from combining positive and negative scores for a given standardized emotion element and assessing whether the resultant score exceeds a previously established certainty threshold representing a minimal certainty required before an emotion element is established (and standardized emotion datum 126 for that element is generated).

Different techniques can be used by the sensory aggregator 132 to handle conflicting inputs 124. For example, in one embodiment, when conflicts exist conflicting inputs 124 having low corresponding weights can be discarded. In another embodiment, only inputs expected to have a high correspondence (e.g., heart rate and respiratory rate, for example) can trigger a conflicting situation, when an expected correspondence is lacking in which case conflicting inputs 124 can be discarded from computations (all other inputs 124 being evaluated by aggregator 132). Additionally, recent patterns can be taken into consideration by the sensory aggregator 132. For example, sudden changes in input values 124 can be critiqued to determine if the change indicates a shift in an emotion of the user 105, which can be highly significant or can indicate an existence of a data abnormality which should be largely ignored.

Additionally, since results produced by the sensory aggregator 132 can be used for different purposes, different configurable modes can exist, which produce different results 126. For example, one processing mode can bias sensory aggregator 132 to generate a relatively smooth set of emotions that gradually transition over time. Such a mode may be preferred by a consumer 134 wanting data 126 indicative of general emotional states of a user 105, but wishing to minimize dramatic emotional shifts (e.g., such a mode can minimize emotional "thrashing"). One way of implementing such a mode is to establish relatively high variance thresholds for the aggregator 132 and/or to implement a smoothing function, where emotional datum 126 are only reported when consist for a set duration and when a very high level of confidence in the accuracy of the datum 126 exists. In contrast, a different processing mode can encourage rapid reporting of user 105 emotional shifts, which may be significant/anticipated when user 105 is being intentionally presented with output designed to elicit an emotional response. In general, the sensory aggregator 132 can be implemented in a highly flexible and configurable manner to generate output 126 suitable for needs of different emotion data consumers 134.

In one embodiment, generated emotion datum 126 can be normalized for standard values. The standard values can be collected from data of several users. In one configuration, standard values themselves can be based upon historical data obtained from a sample set of users connected to sensory capture devices 110. This historical data can be analyzed for patterns. The historical data can optionally be continuously collected, updated, and analyzed so that the standard values themselves and patterns associated with these values evolve over time. A best-fit baseline based upon the standard values can be initially used as a starting point for a user 105, where this starting point can be optionally tuned over time. That is, user 105 specific attributes can be recorded and adjusted for during aggregator 132 processes.

In one embodiment, user 105 specific attributes can be continuously updated using a learning algorithm, so that for a given user 105 accuracy of the generated datum 126 should increase over time. In another embodiment, instead of implementing a learning algorithm, a calibration algorithm can be used, where a system is initially calibrated for a specific user 105 to improve accuracy, but where the system does not necessary dynamic adapt (learn) to user 105 specific idiosyncrasies over time. A calibration state can even vary from session to session, assuming that input 124 varies in a relatively consistent manner depending upon different moods of the user 105 (which the calibration determines).

Although possible to produce emotion adjusted output 128 for display (via device 135) to a user 105, such a step is optional. In some instances, for example, user 105 emotion data 126 can be captured (possibly without explicit user 105 involvement/knowledge) for use in studies (i.e., marketing or psychology studies concerned with user emotion responses to computer presented stimuli) or for business purposes (i.e., call center responses can be transferred away from agents exhibiting hostile emotions when engaged in service calls).

Emotion adjusted output 128 has a wide variety of application areas. For example, users participating in any virtual environment, such as Web based social networking sites, virtual communities (e.g., SECOND LIFE, OPEN SIM, any Massively Multiplayer Online Role-Playing Game (MMORPG), etc.) can communicate, where communications are laden with automatically determined and dynamically changing emotional expressions. Marketing and/or advertising firms can capture and process emotional data from a focus group exposed to a possible advertisement to obtain quantified data indicative of the advertisements success from an emotional perspective. People with physical/medical conditions, which make expression of emotions challenging, can better express their emotions through machine translation achievable via this disclosure.

Numerous embodiments, including networked embodiment 151 and stand-alone embodiment 150, exist for transforming the raw sensory input 122 to produce the standardized emotion data 126 using one or more computing devices executing computer code products. In networked embodiment 151, a user interactive computing device 152 can be linked to sensory capture devices 110, which generate the raw sensory input 122. The raw sensory input 122 can be conveyed over a network 105 to zero or more channel processing servers 154, each including an in-channel processor 130. Channel processed input 124 can be conveyed over network 105 to an aggregation server 156 running sensory aggregator 132. One or more application servers 158, each executing an emotion data consumer 134 computer program product can consume standardized emotion data 126. The application server 158 can interface with the user interactive computing device 152 over network 105. Input and output (including emotion adjusted output 128) can be directly conveyed between the user interactive computing device 152 and the application server 158. Embodiment 151 is just one contemplated networked embodiments—others exist.

Optional use of remotely located networked resources for channel specific processes provides a capability to offload intensive computing operations to specialized devices. For example, facial analysis and speech analysis to ascertain an emotion of a user can both be resource intensive analysis operations, which can be handled by a server (e.g., server 154) having sufficient resources dedicated to that type of analysis. An ability to use networked devices to off-load processing tasks also permits a commoditization of one or more functions described herein as a software service. Thus, a competitive marketplace of services for ascertaining emotions of a user can arise, where providers compete to provide sensory channel specific processing 130, output customizations 128 based on standardized emotion data 126, and/or channel aggregation (e.g., sensory aggregator 132) services. When network options are used during an embodiment of the disclosure, user specific settings for emotion interpretation (per channel and/or in aggregate) can be centrally maintained and utilized regardless of which of many end computing devices (e.g., user interactive computing device 152) a user 105 is using.

In one embodiment, implementation specifics of the network embodiment 151 can conform to a service oriented architecture (SOA). That is, a loose coupling of services with operating systems, programming languages, and other technologies that underlies applications (e.g., emotion data consumers 134) can exist for processing and aggregating sensory input within sensory channels 120 to generate emotion data 126 and to produce emotion adjusted output 128. For example, the functions of the in-channel processor 130, sensory aggregator 132, and other functions described herein (for example, selecting a channel for handling an type of sensory input and routing the input accordingly, as shown by items 315 and 320 of FIG. 3) can be implemented as distinct units of services. Developers can make these services accessible (such as via a Universal Description, Discovery and Integration (UDDI) repository or other service directory), where other developers can reuse and/or modify the services. The service can communicate with each other by passing data from one service to another and/or by coordinating activity between two or more services. In one embodiment, the SOA used to implement the functions described herein can conform to an open standard. For example, at least a portion of the functions described herein can be implemented in a standards based fashion within a JAVA 2 ENTERPRISE EDITION (J2EE) application server, such as an IBM WEBSPHERE server.

Despite many possible advantages offloading some processing to a network, stand-alone embodiments (e.g., embodiment 150) are possible using techniques described herein. Stand-alone (or partially stand alone) capabilities can be beneficial in many situations (i.e., when a device 152 is offline; when configurable settings restrict access to emotion laden information, etc.). In stand-alone embodiment 150, a user interactive device 152 can include in-channel processor 130, sensory aggregator 132, and an emotion data consumer 134.

Each computing device 152, 154, 156, 158 of FIG. 1 can be implemented as one or more computing devices (e.g., includes stand-alone as well as distributed computing devices) which is shown as computing device 160. The computing device 160 can include physical devices and/or virtual devices (implementing in a layer of abstraction over hardware using virtualization techniques). Device 160 can execute computer program products, which include software and firmware 170, using underlying hardware 162. The hardware 162 can include a processor 164, a volatile memory 165, and a non-volatile memory 166 linked via a bus 167. Additional components, such as network interface cards/ports (not shown), can be included in the hardware 162. For example, hardware 162 of the user-interactive computing device 152 and/or devices connected to network 105 geographically proximate to user 105 can include one or more sensory capture device 110 and/or can include a port linked to a sensory capture device 110. The port can include a wired or wireless linkage for exchanging data. Wired ports can include, but are not limited to, a universal serial bus (USB) port, a serial port (e.g., keyboard, mouse), a parallel port (e.g., a parallel printer port), a firewire port, and the like. Wireless ports can include wireless transceivers conforming to a BLUETOOTH, WIRELESS USB, ZIGBEE, WIFI, or other wireless data exchange standard.

The software/firmware 170 can optionally include an operating system 172 upon which applications 173 execute. Thus, a device 160 can be a general purpose device hosting/running emotion transformation specific computer program products. In another embodiment, device 160 can be a special purpose device lacking a discrete operating system 172. Instead, the device 160 can be dedicated (purposed) for a single purpose, such as performing in-channel processing or sensory aggregation in a highly optimized manner. Whether implemented on top of an operating system 172 or not, the applications 173 can include, but are not limited to, in-channel processor 130, sensory aggregator 132, and/or emotion data consumer 134.

Each sensory capture device 110 can produce sensory input 122. The sensory input 122 can include physiological data 189, user input 181, and environmental input 185. Physiological data 189 can include human physiological data of user 105, which can include to measurement of taken from a system of a human body (e.g., cardiovascular system, muscular system, circulatory system, nervous system, respiratory system, excretory system, endocrine system, digestive system, and the like). Further, physiological data 189 can include data from the fields of biochemistry, biophysics, biomechanics, and the like. Physiological data 189 can be obtained from a physiological sensor 188.

Physiological sensors 188 can include any device or peripheral able to capture data specific to a body of user 105, which can be invasive or non-invasive as well as active or passive. Physical sensors 188 can include, but are not limited to, blood pressure sensors (e.g., sphygmomanometer), pulse detector, brain-wave (P300, Mu, Alpha, etc.) sensors (e.g., electroencephalography sensor, magnetoencephalography sensor, hemoencephalography sensor, etc.), electromyography sensors, skin response sensors, fluid sensors (e.g., blood metabolite, oxygen saturation in body tissues sensors, etc.) skin temperature sensors, respiration sensors, conductive ink and textile sensors, and the like.

Environmental input 185 can include data passively obtained from an environment proximate to the user 105. For example, environmental input 185 can include images, video, and audio captured by an audio/video capture device 184. Environmental input 185 can also include an environmental temperature of an environment proximate to the user 105, input from pressure sensors/scales, motion sensor input, and the like. In one embodiment, the environmental input 185 can include images/video of a face of a user 105, which is processed to discern a facial expression of the user 105. Other body language interpretation analytics can also be performed to determine sensory input (i.e., body language can be analyzed to determine if user 105 is nervous, calm, indecisive, etc.). Environmental input 185 can include speech analyzed for voice patterns indicative of emotions of the user 105.

User input 181 can include information intentionally and manually entered by a user 105 using a user input peripheral 180 (e.g., mouse, joystick, keyboard, microphone, touch pad, etc.) In one embodiment, metadata of the user input 181 can be evaluated to determine emotions of user 105 (e.g., typing pattern analysis, hand steadiness when manipulating a joystick/pointer, etc). In another embodiment, semantic content of the user input 181 can be analyzed to ascertain emotions of user 105.

The different inputs 122 (including inputs 181, 185, 189) can be combined within a single sensory channel 120 to accurately determine a given emotional dimension (associated with a channel 120) of a user 105. For example, one channel 120 or emotional dimension can be for semantically analyzed content of input 181, another emotional dimension can be for facial/body analysis results, another emotional dimension can be for voice analysis results, another for respiratory sensor results, another for brain signal results, another for muscular analysis results, another for circulatory results, another for excretory system results, and the like. The actual categories established for each emotional dimension are able to vary. It can be significant, however, that each emotional dimension (associated with a discrete sensory channel 120) be defined, so that sensory input 122 can be processed in a channel specific fashion. This permits channel processed input 124 to be generated, which is abstracted from specifics of the sensory capture device 110 and which may be normalized in a user 105 independent fashion. Thus, channel processed input 124 can be handled in a uniform manner by the sensory aggregator 132.

To elaborate upon the inputs 122 by example, one potential input 122 can include a heart rate input, which is a type of physiological data 189. A heart rate monitory (device 110; sensor 188) can consist of two parts, a transmitter attached to a belt worn around a chest of user 105 and a receiver worn around the wrist of the user 105. As the user's heart beats, an electrical signal, which is detected through the skin via the chest belt, can cause the heart muscle to contract. The belt can transmit an electromagnetic signal containing heart rate data to the wrist receiver, which displays the heart rate to a user. This data can also be fed into a communicatively linked computing device 160, which sends the heart rate data (possible after pre-processing it) to a suitable in-channel processor 130 for handling.

In another example, the input 122 can include a measurement of electrical activity produced by the brain of the user 105, as recorded by electronics of an electroencephalography device (EEG) (e.g., device 110; device 188) positioned proximate to the user's scalp. The electrical signals of the user's brain can be present at a microvolt level, which are amplified using the EEG. The amplified signals can be digitized and conveyed as input 122 to in-channel processor 130.

In still another example, the input 122 can include voice input, which is processed in accordance with a set of one or more voice recognition and/or voice analysis programs. The voice input can be semantically processed for key words and/or phrases indicative of a corresponding emotion. Voice levels, pitches, inflections, speaking rate, and the like can also be analyzed to discern emotions of the speaker (e.g., user 105). The input 122 examples above are provided as illustrative examples only, and are not intended to be limiting.

In FIG. 1, network 105 can include any hardware/software/ and firmware necessary to convey digital content encoded within carrier waves. Content can be contained within analog or digital signals and conveyed through data or voice channels and can be conveyed over a local area network (LAN) or a wide area network (WAN). The network 105 can include local components and data pathways necessary for communications to be exchanged among computing device components and between integrated device components and peripheral devices. The network 105 can also include network equipment, such as routers, data lines, hubs, and intermediary servers which together form a packet-based network, such as the Internet or an intranet. The network 105 can further include circuit-based communication components and mobile communication components, such as telephony switches, modems, cellular communication towers, and the like. The network 105 can include line based and/or wireless communication pathways.

Each of the computing devices 152-158 can include and/or be communicatively linked to one or more data stores. Each data store can be physically implemented within any type of hardware including, but not limited to, a magnetic disk, an optical disk, a semiconductor memory, a digitally encoded plastic memory, a holographic memory, or any other recording medium. The data stores can be a stand-alone storage unit as well as a storage unit formed from a set of physical devices, which may be remotely located from one another. Additionally, information can be stored within each data store in a variety of manners. For example, information can be stored within a database structure or can be stored within one or more files of a file storage system, where each file may or may not be indexed for information searching purposes.

Figure 2:
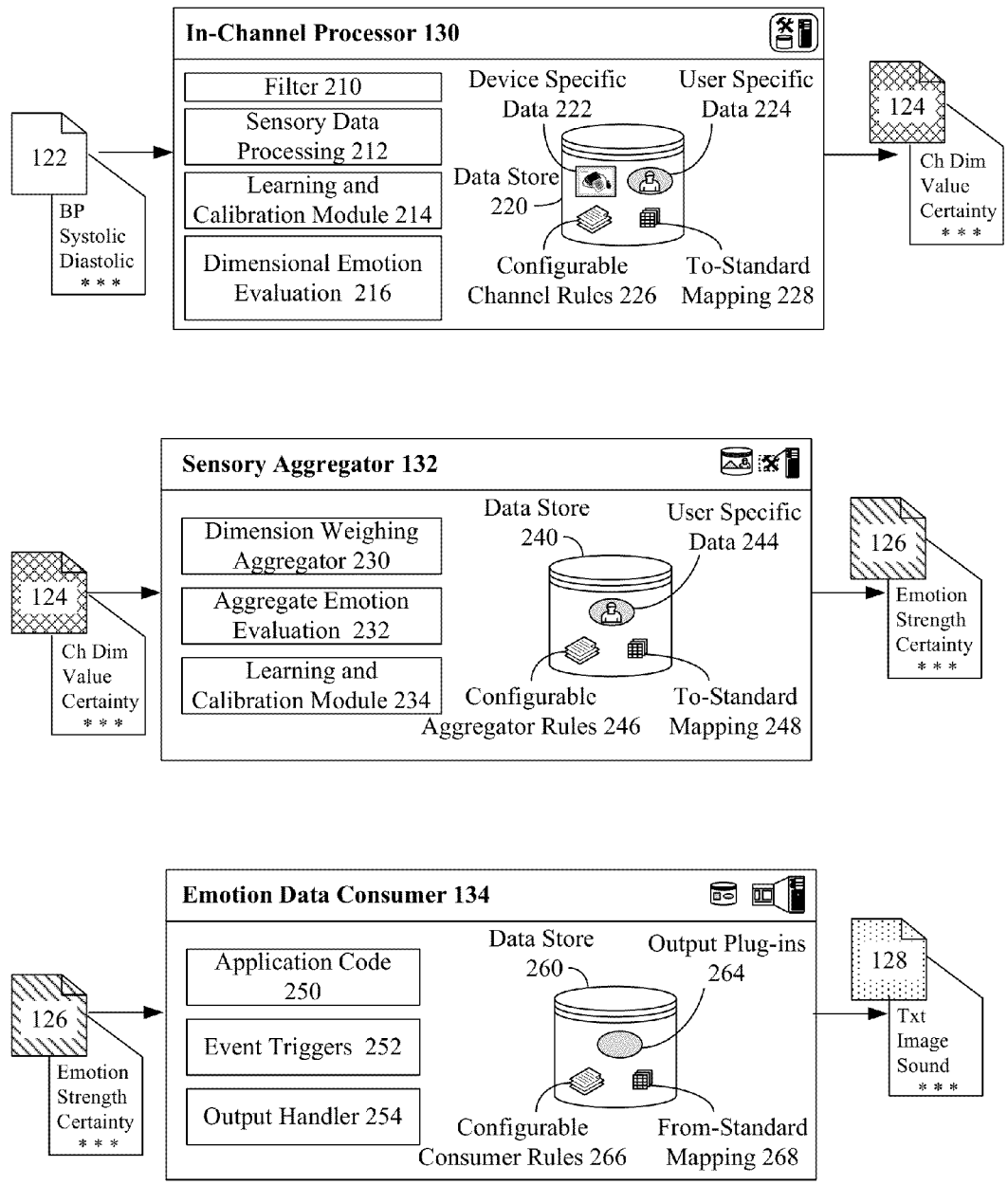
FIG. 2 provides further details for operations performed by an in-channel processor, a sensory aggregator, and/or an emotion data consumer in accordance with an embodiment of the inventive arrangements disclosed herein.

FIG. 2 provides further details for operations performed by the in-channel processor 130, the sensory aggregator 132, and/or the emotion data consumer 134 in accordance with an embodiment of the inventive arrangements disclosed herein. Details provided in FIG. 2 include specifics for one contemplated implementation of the components and/or elements of FIG. 1. FIG. 2 is not to be construed as limiting the disclosure in any manner, and alternative implementation elements consistent with the scope of the claims presented herein are to be considered within scope of this disclosure.

Data shown in FIG. 1 includes sensory input 122, channel processed input 124, standardized emotion datum 126, and emotion adjusted output 128. Although each input and output 122-128 of FIG. 1 includes sample values, these values are included for illustrative purposes and are not to be construed to limit a scope of this disclosure. For example, although the sensory input 122 is shown as being a data instance for blood pressure, which includes a systolic and diastolic measure, a variety of other sensory input 122 types can be handled by processor 130, as previously described.

The input/output 122-128 can include numerous attributes defining a data instance. These attributes can include an input category, name/identifier, a value, strength, a certainty, and the like. These attributes can be defined by a known standard, and can be extensible. Further, the input/output 122-128 specific attributes can be encoded and conveyed among devices using standardized formats, such as being XML encoded and conveyed via TCP/IP based protocols.

In channel processor 130 can include a filter 210, a sensory data processing component 212, a learning and calibration module 214, a dimensional emotion evolution component 216, a data store 220, and/or other such components. The data store 220 can include device specific data 222, user specific data 224, configurable channel specific rules 226, and mappings to a specific standard 228 to which the generated processed input 124 conforms.

The filter 210 can adjust input 122 before it is processed by component 121. These adjustments can include, but are not limited to, sampling input 122, analog-to-digital converting input 122, pre-processing input 122, format converting input 122, etc.

The sensory data processing component 212 can transform a raw value into score/value usable by processor 130. The score generated by component 212 can be device independent, which has been adjusted using device specific data (for a sensory capture device 110). The score can also be adjusted for a specific user based upon user specific data 224. Thus, user specific abnormalities present in data 122 can be removed and/or taken into account.

For example, when the processed input 122 is voice input, user specific language, dialect, grammar patterns, and speech characteristics can be included in data 224 and used by a speech to text converter and/or a speech pattern analyzer (both being instances of processing component 212). In another example, the processed input 122 can include image data that can be analyzed for patterns (by processing component 212) to determine emotions from a user's facial expressions (which can use user specific data 224 to increase accuracy).

In one embodiment, a set of configurable channel rules 226 can be established. These rules 226 can be used to adjust behavior of the sensory data processing component 212. The rules 226 can be user/administrator defined, sensory capture device 110 specific, as well as application (e.g., emotion data consumer) specific.

The learning and calibration module 214 can adjust values of the processor 130 to improve accuracy over time. The values can be part of an automated feedback cycle, which results in a learning capability for the processor. For each user, historical data 122, 124 can be maintained. This historical data can be analyzed for patterns to ascertain a likelihood of emotions being correctly and/or incorrectly evaluated. Sensory data processing 212 parameters, channel rules 226, and other datum can be tuned based on the historical data to improve an accuracy of the channel processed input 124 for a specific individual. In one embodiment, a specific training routine can be implemented, which feeds a known set of test data for a user and having a known set of desired results specific to the user into the in-channel processor 130, which results in the module 214 tuning processor 130 for user specifics.

The dimensional emotion evaluation component 216 converts a score/value computed by the processing component 212 into a standardized value/form. Component 216 can use to-standard mapping data 228. In one embodiment, component 216 can permit use of data obtained from a source not conforming to a desired standard (e.g., information from a standard non-compliant Web site, for example) into a standardized value of channel processed input 124.

Sensory aggregator 132 can include a dimension weighing aggregator 230, an aggregate emotion evaluation module 232, a learning and calibration module 234, a data store 240, and/or other such components. The data store 240 can include user specific data 244, configurable aggregator rules 246, and mappings to a specific standard 248 to which the standard emotion datum 126 conforms.

The dimension weighing aggregator 230 can weigh different emotion dimensions differently relatively to each other. In one embodiment, a user data set including user specific data 244 can be established which permits the weighing to occur in a user specific manner. For example, some humans facial expressions are more easily and accurately read than others, so aggregator 230 can adjust weights based upon user specific data 244 accordingly.

The aggregate emotion evaluation module 232 can include or more algorithms. In one embodiment, code of the module 232 can be adjusted/changed based upon configurable aggregator rules 246. Different algorithms/computations can be more accurate than others based upon human-to-human variances, which module 232 can adjust for driven by data 244. The to-standard mapping 248 data can be used to transform an internal representation of emotion datum to a defined standard. In one embodiment, aggregator 132 can adjust for multiple different standards (or to changes in standards) using mapping data 248 of the relevant standards/standard changes.

The learning and calibration module 234 can adjust values of the aggregator 132 to improve accuracy over time. The values can be part of an automated feedback cycle, which results in a learning capability for the aggregator 132. For each user, historical data 124, 126 can be maintained. This historical data can be analyzed for patterns to ascertain a likelihood of emotions being correctly and/or incorrectly evaluated. Weighing (230) and aggregating (232), aggregator rules 246, and other parameters can be tuned based on the historical data to improve an accuracy of the standard emotion datum 126 for a specific individual. In one embodiment, a specific training routine can be implemented, which feeds a known set of test data for a user and having a known set of desired results specific to the user into the sensory aggregator 132, which results in the module 234 tuning aggregator 132 for user specifics.

Emotion data consumer 134 can include application code 250, event triggers 252 tied to emotion datum values, output handler 254, data store 260 and/or other such components.

The data store 260 can include output plug-ins 264, configurable consumer rules 266, and mappings 268 from a defined standard to application specific actions.

The application code 250 of the emotion data consumer 134 can be specific to a particular application, such as an IM client/server application, a virtual world application, a social networking application, and the like. Event triggers 252 can be linked to the application code 250, which respond to information contained in standardized emotion datum 126. For example, when a given emotion has a strength and certainty greater than a defined threshold, programmatic actions of the application code 250 can be triggered.

The output handler 254 can alter application output based upon datum 126. For example, handler 254 can generate text, images, sounds, and the like that correspond to a given emotion datum 126 which are applied to an application context (e.g., is programmatically linked to code 250).

The plug-ins 264 can provide a means for extending actions taken by consumer 134 responsive to the standardized emotion data 126. For example, an output plug-in 264 can adjust an avatar's displayed image from a standard image set to a set of images having customized facial expressions dynamically adjusted to correspond to the data 126. Similarly, the configurable consumer rules 266 can permit users/administrators to adjust behavior of application code 250 and/or output handler 254 in a tailored manner. In one embodiment, the consumer 134 can be capable of accepting standards based emotion datum 126 for more than one standard. The from-standards mapping 268 can be modified to permit consumer 134 to respond to these different standards and/or changes in a single standard handled by consumer 134.

Figure 3:
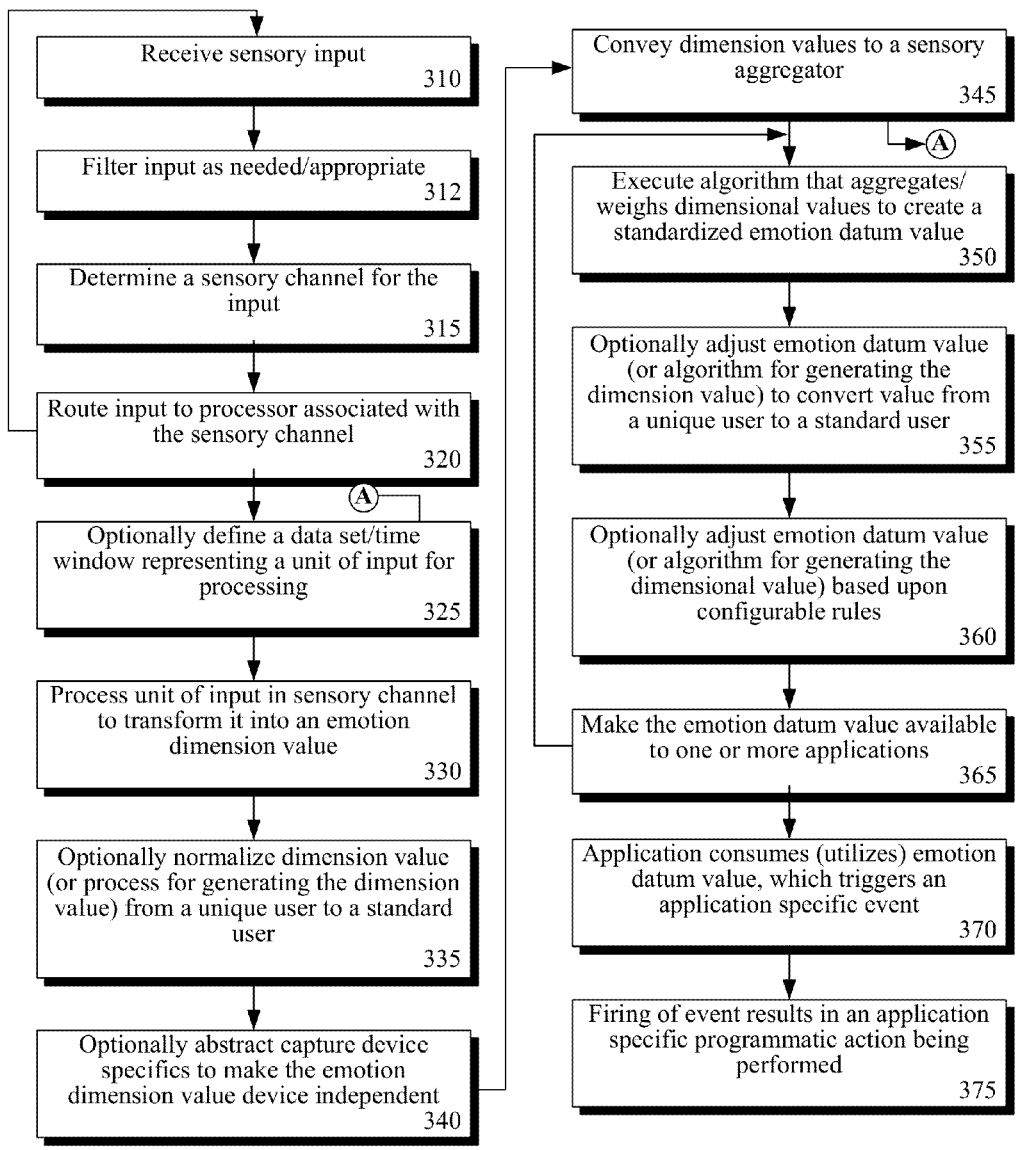
FIG. 3 is a flow chart of a method for processing sensory input through multiple sensory channels to generate standardized emotion datum values in accordance with an embodiment of the inventive arrangements disclosed herein.

FIG. 3 is a flow chart of a method 300 for processing sensory input through multiple sensory channels to generate standardized emotion datum values in accordance with an embodiment of the inventive arrangements disclosed herein. Method 300 can be performed in context of a system shown in FIG. 1 and FIG. 2 and/or performed in context of any other suitable computing environment. In method 300, one or more sensory capture devices can receive sensory input from a user. The captured sensory input can include physiological data from a physiological sensor as well as environmental input and/or user input.

In step 310, the captured sensory input can be received by a computing device. In step 312, the sensory input can be optionally filtered as needed and/or appropriate. The filtering can occur locally on a device and can remove anomalous input at its source, so that it is not processed within a sensory channel. In one embodiment, local pre-processing actions can occur in addition to and/or instead of the filtering. The pre-processing can, for example, digitize, sample, aggregate, average, and otherwise adjust the raw sensory input before it is sent in-channel for processing.

In step 315, a sensory channel for the received input can be determined. Different standards-defined types of sensory channels can exist, where each is dedicated to handle a specific emotional dimension. An emotional dimension can correspond to one or more defined types or categories of sensory input. The input can be routed to a processor associated with the determined sensory channel, as shown in step 320. Input can be continuously received, which is shown by the flow of the method 300 selectively branching from step 320 to step 310.

After sensory input has been routed, the receiving processor can optionally define a processing unit, which is a set of data (such as a time window of data) to be analyzed, as shown by step 325. In one embodiment, the processing unit can include a single value. In other embodiment, the processing unit can include two or more input values.

In step 330, the unit of input can be processed in the sensory channel to transform the unit of input into an emotion dimension value. In step 335, the emotion dimension value can be optionally normalized from a unique user specific value to a standard user value. In one embodiment, this normalization can represent an adjustment of the process or algorithm that generates the dimension value, as opposed to being a post processing of the dimension value to achieve a substantially equivalent result. In step 340, capture device specifics can be optionally abstracted to make the emotion dimension value a device independent one. This abstraction can occur within code of an algorithm that generates the emotion dimension value, or as a pre or post processing step.

The generated emotion dimension value, which has been generated and/or processed within a sensory channel to this stage, can be conveyed to a sensory aggregator. Input can be continuously processed within sensory channels and dimension value can be continuously sent to a sensory aggregator, which is expressed by method 300 selectively proceeding from step 345 to step 325.

In step 350, after a sensory aggregator has received dimension values from multiple channels, an algorithm can execute that aggregates/weighs dimensional values to create a standardized emotion datum value. In optional step 355, the emotion datum value can be converted from a value unique to a user to a standardized value that is user independent. In optional step 360, the emotion datum value can be adjusted based upon configurable rules. Either of the steps 355 or 360 can be performed within code of the algorithm that generates the emotion datum value and/or can be performed as a pre or post processing step. After it is generated, the emotion datum value can be made available to one or more applications, as shown by step 365. The process that generates the emotion datum value can be continuous, which is shown by the method 300 flow proceeding from step 365 to step 350.

One or more applications can respond to the emotion datum values, as these values are generated and made accessible. In step 370, one or more of these application can consume (or utilize) these emotion datum values. These values can be programmatically linked to application specific events. The firing of these events can result in application specific programmatic actions being preformed, as shown by step 375.

The programmatic actions can, for example, generate output (viewable by one or more users) which communicates an emotion of the user from whom the sensory input was captured to one or more other users. The programmatic actions can, in another example, alter logic of an application with which a user interacts in reaction to an emotion condition of a user. For instance, in a call center environment, emotions of agents can be monitored/determined and calls can be automatically routed to other agents (based upon code of a call center application responding to emotion triggered events) whenever one agent becomes agitated, angry, or experiences another emotion that may be detrimental to professional handling of a call.

Method 300 can include additional and/or alternative processing steps not explicitly shown in FIG. 3. For example, although not expressed in FIG. 3, the method 300 can include a learning and calibration step, where an in-channel processor and/or aggregator can be trained/calibrated to increase processing accuracy. The processing of method 300 can be designed to occur in real-time, near real-time, and/or after appreciable processing delays depending upon implementation specifics.

The diagrams in the FIGS. 1-3 illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A system for incorporating human emotions in a computing environment comprising:
   one or more processors, and a memory storing computer readable program code;
   a plurality of discrete sensory channels each for handling sensory input detected via one or more sensors, each of the one or more sensors comprising hardware, wherein different senses are associated with different ones of the discrete sensory channels, wherein each of the discrete sensory channels is a sensory channel corresponding to a specific emotion dimension, wherein sensory input handled within the sensory channels comprises physiological input providing a physiological measurement from a body of the user;
   a plurality of in-channel processors, each being one of the one or more processors, that process sensory input specific to the channel and that generate emotion dimension values from the sensory input, wherein each emotion dimension value has been transformed to be independent of idiosyncrasies of a sensory capture device from which the sensory input was originally obtained; and
   a sensory aggregator, implemented in the computer readable program code stored in the memory and executable by at least one of the one or more processors, for aggregating emotion dimension values generated in a per-channel basis by the in-channel processors to generate at least one emotion datum value, which is a value for an emotional characteristic of a user from whom the sensory input was gathered, and is an application independent value that is able to be utilized by a plurality of independent applications to discern emotions of said user and to cause application specific code of the independent applications to be reactive to changes in sensory aggregator generated emotion datum values.

2. The system of claim 1, further comprising:
   a plurality of sensory capture devices, wherein said sensory capture devices comprise a physiological sensor, an audio or video capture device, and a user input peripheral for manual user input, wherein input obtained from the physiological sensor, from the audio or video capture device, and from the user input peripheral is handled by separately by different ones of the discrete sensory channels, and wherein said physiological sensor obtains a measure from a system of the human body selected from a group of systems consisting of a cardiovascular system, a muscular system, a circulatory system, a nervous system, a respiratory system, an excretory system, an endocrine system, and a digestive system.

3. The system of claim 1, further comprising:
   a plurality of emotion data consumers each performing a programmatic actions driven by emotion datum values generated by the sensory aggregator.

4. The system of claim 3, wherein at least one of the emotion data consumers comprises a virtual world software application in which a plurality of humans interact though user specific avatars, wherein said user specific avatars express emotions corresponding to emotions of their users driven by the emotion data values.

5. The system of claim 1, wherein at least a portion of the in-channel processors are computer program products hosted by a physical computing device remotely located and connected by network to another physical computing device from which the sensory input handled by the portion of the in-channel processors originated.

6. The system of claim 1, wherein at least one of the in-channel processors analyzes speech input to determine emotions of the user who provided the speech input based upon vocal characteristics of the speech input, and wherein at least one of the in-channel processors analyzes images to determine facial expressions of the user.

7. The system of claim 1, wherein said in-channel processors and said sensory aggregator are components of a service oriented architecture (SOA), where software services are provided for processing said sensory input and for aggregating said emotion dimension values.

8. A system comprising:
   one or more processors;
   one or more non-transitory storage mediums storing program instructions, said one or more processors executing the program instructions to:
   receive a plurality of sensory inputs of a user;
   process each sensory input in a unique one of a plurality of sensory channels, each sensory channel corresponding to a specific emotion dimension, wherein said processing comprises transforming the physiological measurement into an emotion dimension value, said emotion dimension value;
   aggregate the emotion dimension values from each of the sensory channels to generate at least one emotion datum value, which is a value for an emotional characteristic of said user, wherein said emotion datum value is an application independent value that is utilized by a plurality of independent applications to discern emotions of said user and to cause application specific code of the independent applications to be reactive to changes in sensory aggregator generated emotion datum values when aggregating the emotion dimension values, adjust user specific factors specified within a stored user specific data set to normalize the generated emotion datum value to a baseline of an average person; and
   provide the emotion datum value to the independent applications, wherein each of the independent applications perform a programmatic action driven by the emotion datum value.

9. The system of claim 8, wherein said user is interacting with a graphical user interface to participate within a virtual environment in which said user is represented in said virtual environment as an avatar, which is presented to a plurality of other users of said virtual environment, wherein a presentation characteristic of said avatar is adjusted for the emotion datum value so that an emotion corresponding to the emotion datum value is presented to the other users.

10. The system of claim 9, wherein the presentation characteristic alters at least one of a facial expression of the avatar and a speech characteristic of the avatar in accordance with the emotion corresponding to the emotion datum value.

11. The system of claim 8, wherein the emotion datum value is generated without the user ever explicitly manually inputting semantic content for an emotion.

12. The system of claim 8, wherein a plurality of independent applications are able to consume the emotion datum value to drive application specific changes based upon emotions of the user.

13. The system of claim 8, wherein said user participates in an application session of an application which performs said programmatic action driven by the emotion datum value, wherein during the application session, the plurality of sensory inputs from the user are continuously received, processed, and aggregated to continuously generate different emotion datum values, which drive programmatic actions of the application that are based upon emotional variances of the user during the application session, wherein the continuous receiving, processing, aggregating, and performing of the programmatic actions occur in at least one of real-time and near real time, wherein the application session is a communication session in which said user communicates in real-time or near real-time with at least one other user, wherein during said communication session said other user is continuously appraised of emotional changes of said user determined from the continuously generated emotion datum values.

14. The system of claim 8, wherein processing for different ones of the plurality of channels is handled by different networked computing devices, each of the different networked computing devices being explicitly dedicated to handle at least one specific sensory channel specific processing task.

15. The system of claim 8, wherein the one or more processors further execute the program instructions to:
collect historical data for said user comprising emotion data of the user;
analyze said historical data on an iterative basis; and
adjust parameters used to generate said emotion datum value in accordance with results of said analyzing to improve an accuracy of the generated emotion datum value over time, thereby instituting a learning process to continuously improve method produced results in a user specific manner.

16. The system of claim 8, wherein the one or more processors further execute the program instructions to:
collect channel specific historical data for said user on a sensory channel specific basis for each of said plurality of sensory channels;
analyze said channel specific historical data for each sensory channel on an iterative basis;
adjust parameters used to generate said emotion dimension values in accordance with results of said analyzing of the channel specific historical data to improve an accuracy of the generated emotion dimension values over time; and
collect aggregation specific historical data for said user comprising emotion datum values and emotion datum values generated from said emotion datum values;
analyze said aggregation specific historical data on an iterative basis; and
adjust parameters used to generate said emotion datum values in accordance with results of said analyzing of the aggregation specific historical data to improve an accuracy of the generated emotion datum values over time.

17. The system of claim 8, wherein the one or more processors further execute the program instructions to:
query an emotional data set specific to said user, wherein said emotion data set weights the dimension values relative to each other to generate the emotion datum value in a user specific manner that accounts for a user specific point in a human emotional variance range.

18. The system of claim 8, wherein the processing of each sensory input is performed as a software service by a computing device remotely located from a computing device proximate to the user, and wherein the aggregating of the emotion dimension values is performed as a software service by a computing device remotely located from a computing device proximate to the user.

19. A system comprising:
one or more processors;
one or more non-transitory storage mediums storing program instructions, said one or more processors executing the program instructions to:
receive a plurality of sensory inputs of a user;
process each sensory input in a unique one of a plurality of sensory channels, each sensory channel corresponding to a specific emotion dimension, wherein said processing comprises transforming the physiological measurement into an emotion dimension value, said emotion dimension value;
aggregate the emotion dimension values from each of the sensory channels to generate at least one emotion datum value, which is a value for an emotional characteristic of said user, wherein said emotion datum value is an application independent value that is utilized by a plurality of independent applications to discern emotions of said user and to cause application specific code of the independent applications to be reactive to changes in sensory aggregator generated emotion datum values;
provide the emotion datum value to the independent applications, wherein each of the independent applications perform a programmatic action driven by the emotion datum value; and
query an emotional data set specific to said user, wherein said emotion data set weights the dimension values relative to each other to generate the emotion datum value in a user specific manner that accounts for a user specific point in a human emotional variance range.

20. The system of claim 19, wherein the one or more processors further execute the program instructions to:
collect historical data for said user comprising emotion data of the user;
analyze said historical data on an iterative basis; and
adjust parameters used to generate said emotion datum value in accordance with results of said analyzing to improve an accuracy of the generated emotion datum value over time, thereby instituting a learning process to continuously improve method produced results in a user specific manner.

* * * * *